(12) United States Patent
Bertolotti et al.

(10) Patent No.: US 7,803,962 B2
(45) Date of Patent: Sep. 28, 2010

(54) PROCESS FOR THE RESOLUTION OF RACEMIC VERAPAMIL

(75) Inventors: Chiara Bertolotti, Ciserano (IT); Massimiliano Lussana, Gorle (IT); Enrica Pizzatti, Poggiridenti (IT); Enrico Vigano', Lurago D'Erba (IT); Ernesto Landonio, Rescaldina (IT)

(73) Assignee: Cosma S.p.A., Ciserano (IT)

( * ) Notice: Subject to any disclaimer, the term of this patent is extended or adjusted under 35 U.S.C. 154(b) by 329 days.

(21) Appl. No.: 12/156,706

(22) Filed: Jun. 3, 2008

(65) Prior Publication Data

US 2008/0306296 A1    Dec. 11, 2008

(30) Foreign Application Priority Data

Jun. 7, 2007 (IT) .......................... MI2007A1160

(51) Int. Cl.
*C07C 255/36* (2006.01)
(52) U.S. Cl. ...................................... 558/354
(58) Field of Classification Search ................ 558/354
See application file for complete search history.

(56) References Cited

FOREIGN PATENT DOCUMENTS

| GB | 1377209 | 12/1974 |
|----|---------|---------|
| WO | WO 93/16035 | 8/1993 |
| WO | WO 95/09150 | * 4/1995 |

OTHER PUBLICATIONS

H. Ramuz, *Synthesis and Absolute Configuration of the Enantiomers of Verapamil*, Helvetica Chimica Acta, vol. 58, Fasc. 7 (1975), Nr. 224, pp. 2050-2060.

* cited by examiner

*Primary Examiner*—Rei-tsang Shiao
(74) *Attorney, Agent, or Firm*—Abelman, Frayne & Schwab

(57) ABSTRACT

A new process is described for the resolution of racemic verapamil, which allows the desired enantiomer to be obtained in high yields and with high enantiomeric purity. The process uses optically active 2,3-bis[(2-fluorobenzoyl)oxy]butanedioic acid as the resolving agent, and a water/dimethylformamide or water/acetonitrile or water/methanol mixture, as the reaction solvent.

11 Claims, No Drawings

PROCESS FOR THE RESOLUTION OF RACEMIC VERAPAMIL

FIELD OF THE INVENTION

The present invention relates to a new industrially highly advantageous process for the resolution of verapamil enantiomers.

STATE OF THE ART

Verapamil, [1,7-bis(3,4-dimethoxyphenyl)-3-methyl-aza-7-cyano-8-methyl-nonane], of formula (I)

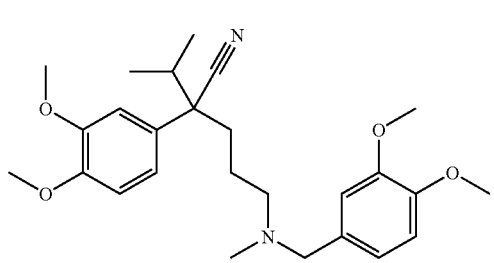

(I)

is a known drug with coronary vasodilator action. The compound has a stereogenic centre, and can hence also be synthesized in enantiopure form. There is an interest in providing single enantiomers, as they have a greater activity and/or selectivity towards specific cardiovascular pathologies. Said enantiomers are accessible by asymmetric synthesis or by resolution of their racemic mixtures, both cases involving problems which are difficultly acceptable on an industrial level.

For example DE-C-20 59 985 describes the synthesis of specific verapamil enantiomers starting from its optically active precursors; said synthesis route requires the use of reagents of high optical purity and of high cost.

On the other hand racemic mixtures of verapamil are notoriously difficult to resolve into single enantiomers (*Helv. Chim. Acta* 58 (1975) 2050).

EP-A-625137 describes a resolution process by means of a reaction between racemic verapamil and optically active dituluoyltartaric acid or dibenzoyltartaric acid: mixture resolution is achieved by the selective crystallization of the corresponding enantiomer from a water/methanol or water/acetone mixture in precise molar ratios.

This process requires three crystallizations of the reaction product and a further crystallization of the optical isomer of the isolated verapamil, to obtain a high optical purity.

SUMMARY

The applicant has now found a new process for the resolution of verapamil which allows the required enantiomer to be obtained in high yields and with a high enantiomeric purity in an extremely simplified manner and hence being less demanding at the industrial level. The process proceeds under conditions which are considerably different from those described in the known art, in particular regarding the resolving agent used, 2,3-bis[(2-fluorobenzoyl)oxy]butanedioic acid, in the optically active form.

DETAILED DESCRIPTION

The present invention relates to the resolution of racemic verapamil into its optical antipodes, by reaction with 2,3-bis[(2-fluorobenzoyl)oxy]butanedioic acid, in the optically active form.

The aforesaid resolving agent is easily obtainable from L-2,3-dihydroxybutanedioic acid or D-2,3-dihydroxybutanedioic acid by known esterification methods, such as reacting said dihydroxybutanedioic acid with 2-F benzoyl chloride or with 2-F benzoic acid in accordance with the following scheme, where R'=OH, Cl.

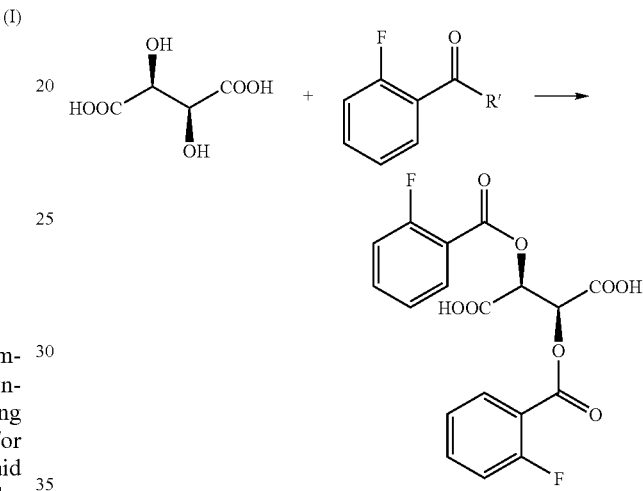

The molar ratio of resolving agent to racemic verapamil is preferably from 1.3:1 to 0.2:1, more preferably from 1:1 to 0.5:1. Particularly preferred is a ratio of 0.85:1. The reaction between the resolving agent and verapamil is a salification reaction. Depending on the optical form of the resolving agent used, one of the two enantiomers of verapamil separates out as an insoluble salt with high yields and very high optical purity, whereas the opposite enantiomer remains in solution. In particular, in order to precipitate the (S)-verapamil enantiomer, (2R,3R)-2,3-bis[(2-fluorobenzoyl)oxy]butanedioic acid is used whereas to precipitate the (R)-verapamil enantiomer, the same acid is used but in the optical form (2S,3S).

The verapamil to be resolved is normally racemic verapamil; however this does not exclude the use of a verapamil already partially enriched in that of the two enantiomers of which a further increase in the degree of enantiomeric purity is desired.

The verapamil is normally used in the form of free base. However it is also possible to start from one of its salts, such as the hydrochloride, then suitably releasing the relative base by alkalizing the solution.

The applicant has also found that the reaction selectivity is influenced by the solvent. Particularly positive results were obtained with a reaction solvent consisting of a water/dimethylformamide or a water/acetonitrile or a water/methanol mixture in specific volume ratios.

In the mixture of the invention, the water and the dimethylformamide are used in a volume/volume ratio from 0.5:1 to 2.0:1, preferably from 0.6:1 to 1.2:1 and more preferably from 0.7:1 to 0.9:1.

In the case of the water and acetonitrile mixture, the ratios are: from 0.6:1 to 2.0:1, preferably from 0.8:1 to 1.2:1; particularly preferred is the ratio 1:1. The water/methanol mixture is preferably used with ratios from 0.2:1 to 0.8:1, preferably from 0.3:1 to 0.6:1; particularly preferred is the ratio 0.5:1.

The weight/volume ratio (g/cc) of verapamil to the aforesaid solvent mixtures is preferably from 0.05:1 to 0.20:1, more preferably from 0.07:1 to 0.17:1.

The salification reaction with the resolving agent is carried out at a temperature between 55 and 70° C., more preferably between 60 and 65° C., then leaving the mixture to cool to ambient temperature.

A non-limitative manner of conducting, the process is as follows: a water/dimethylformamide or water/acetonitrile or water/methanol mixture in the aforesaid ratios is prepared and placed in a suitable reactor. The verapamil and the resolving agent are then added. The addition order of said reagents is not crucial and can be suitably varied: for example all the solid components can be dry fed into the reactor, then finally adding the previously prepared mixture of solvents; in place of the preformed mixture the two solvents can also be added separately in the necessary proportions to form the mixture.

In case of starting from a verapamil salt solution (instead of the free base), the process comprises a further step, consisting in the treatment of the verapamil salt with an alkali (e.g. 30% NaOH) which regenerates the corresponding free base, making it available for salification with the resolving agent.

Depending on the reaction conditions, in particular the applied heating/cooling gradient, the salified enantiomer can either precipitate immediately or later, after a suitable agitation and/or decantation. The precipitation can be facilitated using known systems, for example adding a crystal seed of the desired diastereomeric salt.

At the end of the reaction, the selectively precipitated enantiomer is separated from the reaction mixture by filtration or other comparable techniques; the precipitate can be washed once or several times, possibly recrystallized, and dried. From the precipitation mother liquors the opposite verapamil enantiomer can be recovered, by drying or other comparable techniques.

The present process achieves very high yields and enantiomeric purity levels. Should an even greater enantiomeric purity be desired, the precipitate obtained can be subjected to recrystallization.

As previously mentioned the reaction of racemic verapamil with one of the optical antipodes of 2,3-bis[(2-fluorobenzoyl)oxy]butanedioic acid leads to the precipitation of the required optically active verapamil isomer and, in contrast to the prior art which describes at least four crystallizations, it has been possible to achieve a very high enantiomeric purity with one single crystallization.

Furthermore it is evident that on an industrial level each additional crystallization involves hardly acceptable costs in terms of solvent consumption, energy consumption, processing time and hence productivity.

A further surprising aspect of the present invention is due to the fact that attempts made by the applicant to establish a similar process by using the optical isomers of 2,3-bis[(2-chlorobenzoyl)oxy]butanedioic acid have led only to the formation of non-crystallizable and non-separable oils with all the solvents used, in particular with the solvent mixtures that gave the results illustrated below with the optically active isomers of 2,3-bis[(2-fluorobenzoyl)oxy]butanedioic acid.

The following non-limiting examples relating to the preparation of the present invention and illustrating its characteristics are given below.

Experimental Part

EXAMPLE 1

4.6 g of (R,S)-verapamil hydrochloride (MW: 491.07, mol: 0.00937), 2.77 g of (2R,3R)-2,3-bis[(2-fluorobenzoyl)oxy]butanedioic acid (MW: 394.28, mol: 0.00702), 18 cc of water and 23.4 cc of dimethylformamide were introduced into a flask.

30% sodium hydroxide (0.62 g, MW: 40, mol: 0.0046) was added under agitation; the mixture was heated to 65° C. and then left to cool for 12 hours: the product precipitated. After filtration of the precipitate under vacuum and after drying it, 4 g of the crude salt were obtained with an enantiomeric purity of 87.1% as (S)-verapamil.

The crude salt was crystallized from a dimethylformamide/water mixture to provide a salt with an enantiomeric purity=96.8%.

Enantiomeric purity was measured by HPLC separation of enantiomers on a Chiracel OD-R 250×4.6 mm 10 μm chiral column using an Agilent Technologies HP 1100 instrument.

EXAMPLE 2

4.6 g of (R,S)-verapamil hydrochloride (MW: 491.07, mol: 0.0094), 2.77 g of (2R,3R)-2,3-bis[(2-fluorobenzoyl)oxy]butanedioic acid (MW: 394.28 mol: 0.007) 16.6 cc of water and 24.8 cc of dimethylformamide were introduced into a flask.

30% sodium hydroxide (0.62 g, MW: 40, mol: 0.0046) was added under agitation; the mixture was heated to 65° C. and then left to cool for 12 hours: the product precipitated. After filtration of the precipitate under vacuum and after drying it, 3.93 g of the crude salt were obtained (enantiomeric purity=84.17% as (S)-verapamil).

EXAMPLE 3 (COMPARATIVE)

Under similar conditions to those of example 1, (2R,3R)-2,3-bis[(2-chlorobenzoyl)oxy]butanedioic acid was used as an alternative to (2R,3R)-2,3-bis[(2-fluorobenzoyl)oxy]butanedioic acid: an oil was obtained which could not be solidified.

Said "2-chloro" acid, even under all the other conditions tested, gave rise to the formation of gums or oils which could in no way be crystallized.

EXAMPLE 4

23 g of (R,S)-verapamil hydrochloride (MW: 491.07, mol: 0.0468), 13.85 g of (2S,3S)-2,3-bis[(2-fluorobenzoyl)oxy]butanedioic acid (MW: 394.28, mol: 0.03513), 103.5 cc of water and 116.7 cc of dimethylformamide were introduced into a flask.

30% sodium hydroxide (3.1 g, MW: 40, mol: 0.02325) was added under agitation; the mixture was heated to 60° C. and then left to cool for 12 hours: the product precipitated. After filtration of the precipitate under vacuum and after drying it, 20.81 g of the crude salt were obtained (enantiomeric purity=86.5% as (R)-verapamil).

The crude salt was crystallized from a dimethylformamide/water mixture to provide a salt with an enantiomeric purity=97.08%.

EXAMPLE 5

11.5 g of (R,S)-verapamil hydrochloride (MW: 491.07, mol: 0.02342), 6.925 g of (2S,3S)-2,3-bis[(2-fluorobenzoyl)

oxy]butanedioic acid (MW: 394.28, mol: 0.0176), 45 cc of water and 58.5 cc of dimethylformamide were introduced into a flask.

30% sodium hydroxide (1.55 g, MW: 40, mol: 0.0116) was added under agitation; the mixture was heated to 65° C. and then left to cool for 12 hours: the product precipitated. After filtration of the precipitate under vacuum and after drying it, 10.42 g of the crude salt were obtained (enantiomeric purity=87.45% as (R)-verapamil).

The crude salt was crystallized from a dimethylformamide/water mixture to provide a salt with an enantiomeric purity=97.16%.

EXAMPLE 6

63.10 g of (R,S)-verapamil hydrochloride (MW: 491.07, mol: 0.128), 38 g of (2S,3S)-2,3-bis[(2-fluorobenzoyl)oxy]butanedioic acid (MW: 394.28, mol: 0.0964), 247 cc of water and 321 cc of dimethylformamide were introduced into a flask.

30% sodium hydroxide (8.5 g, MW: 40, mol: 0.064) was added under agitation; the mixture was heated to 65° C. and then left to cool for 12 hours: the product precipitated. After filtration of the precipitate under vacuum and after drying it, 53.08 g of the crude salt were obtained (enantiomeric purity=87.93% as (R)-verapamil).

The crude salt was crystallized from a dimethylformamide/water mixture to provide a salt with an enantiomeric purity=95.73%.

EXAMPLE 7

4.6 g of (R,S)-verapamil hydrochloride (MW: 491.07, mol: 0.00937), 2.77 g of (2R,3R)-2,3-bis[(2-fluorobenzoyl)oxy]butanedioic acid (MW: 394.28, mol: 0.00703), 16.1 cc of water and 16.1 cc of acetonitrile were introduced into a flask.

30% sodium hydroxide (0.62 g, MW: 40, mol: 0.0046) was added under agitation; the mixture was heated to 65° C. then and left to cool for 12 hours: the product precipitated. After filtration of the precipitate under vacuum and after drying it, 3.68 g of the crude salt were obtained (enantiomeric purity=81.27% as (S)-verapamil).

EXAMPLE 8

30 g of (R,S)-verapamil hydrochloride (MW: 491.07, mol: 0.0611), 22.86 g of (2S,3S)-2,3-bis[(2-fluorobenzoyl)oxy]butanedioic acid (MW: 394.28, mol: 0.058), 110 cc of water and 220 cc of methanol were introduced into a flask.

30% sodium hydroxide (4.06 g, MW: 40, mol: 0.03) was added under agitation; the mixture was heated to form a solution and then cooled: the precipitated product was filtered off and dried. 28 g of the crude salt were obtained (enantiomeric purity=91.8% as (R)-verapamil).

The crude salt was crystallized from a methanol/water mixture to provide a salt with an enantiomeric purity=99.62%.

The verapamil base was released from the salt using an inorganic base and converted directly into the corresponding hydrochloride. 9.9 g of (R)-verapamil hydrochloride were obtained with an enantiomeric purity=99.66%.

EXAMPLE 9

42.23 g of (R,S)-verapamil hydrochloride (MW: 491.07, mol: 0.086), 28.86 g of (2S,3S)-2,3-bis[(2-fluorobenzoyl)oxy]butanedioic acid (MW: 394.28, mol: 0.073), 154.8 cc of water and 309.7 cc of methanol were introduced into a flask.

30% sodium hydroxide (5.73 g, MW: 40, mol: 0.043) was added under agitation; the mixture was heated to form a solution and then cooled: the precipitated product was filtered off and dried. 37.8 g of the crude salt were obtained (enantiomeric purity=94.0% as (R)-verapamil).

The crude salt was crystallized from a methanol/water mixture to provide a salt with an enantiomeric purity=99.5%.

EXAMPLE 10

30 g of (R,S)-verapamil hydrochloride (MW: 491.07, mol: 0.0611), 20.46 g of (2S,3S)-2,3-bis[(2-fluorobenzoyl)oxy]butanedioic acid (MW: 394.28, mol: 0.0519), 117.5 cc of water and 152.5 cc of dimethylformamide were introduced into a flask.

30% sodium hydroxide (4.06 g, MW: 40, mol: 0.03) was added under agitation; the mixture was heated to 60° C. and then left to cool for 12 hours. The product precipitated.

After filtration of the precipitate under vacuum and after drying it, 28.5 g of the crude salt were obtained (enantiomeric purity=86.0% as (R)-verapamil).

The crude salt was crystallized from a dimethylformamide/water mixture to provide a salt with an enantiomeric purity=97.9%.

The invention claimed is:

1. A process for the enantiomeric resolution of verapamil, characterized in that racemic verapamil is reacted with one of the two optical antipodes of 2,3-bis[(2-fluorobenzoyl)oxy]butanedioic acid, in the presence of a solvent.

2. The process according to claim 1 wherein the racemic verapamil is reacted with (2S,3S)-2,3-bis[(2-fluorobenzoyl)oxy]butanedioic acid to obtain (R)-verapamil.

3. The process according to claim 1 wherein the racemic verapamil is reacted with (2R,3R)-2,3-bis[(2-fluorobenzoyl)oxy]butanedioic acid to obtain (S)-verapamil.

4. The process according to claim 1 wherein the solvent is selected from the group consisting of water/dimethylformamide, water/acetonitrile and water/methanol mixtures.

5. The process according to claim 1 wherein the optically active 2,3-bis[(2-fluorobenzoyl)oxy]butanedioic acid is reacted with the racemic verapamil in a molar ratio from 1.3:1 to 0.2:1.

6. The process according to claim 5 wherein the optically active 2,3-bis[(2-fluorobenzoyl)oxy]butanedioic acid is reacted with the racemic verapamil in a molar ratio from 1:1 to 0.5:1.

7. The process according to claim 1 wherein the racemic verapamil is reacted in a weight/volume ratio from 0.05:1 to 0.20:1 with respect to the solvent.

8. The process according to claim 7 wherein the racemic verapamil is reacted in a weight:volume ratio from 0.07:1 to 0.17:1 with respect to the solvent.

9. The process according to claim 4 wherein the water/dimethylformamide volume ratio is preferably from 0.6:1 to 1.2:1.

10. The process according to claim 4 wherein the water/acetonitrile volume ratio is preferably from 0.81 to 1.2:1.

11. The process according to claim 4 wherein the water/methanol volume ratio is preferably from 0.3:1 to 0.6:1.

* * * * *